US009400284B2

(12) United States Patent
Vigliotti et al.

(10) Patent No.: US 9,400,284 B2
(45) Date of Patent: Jul. 26, 2016

(54) METHOD OF DETECTING A RISK OF CANCER

(71) Applicants: Anthony Sabato Vigliotti, Port Charlotte, FL (US); Salvatore Anthony Vigliotti, Port Charlotte, FL (US)

(72) Inventors: Anthony Sabato Vigliotti, Port Charlotte, FL (US); Salvatore Anthony Vigliotti, Port Charlotte, FL (US)

( * ) Notice: Subject to any disclaimer, the term of this patent is extended or adjusted under 35 U.S.C. 154(b) by 0 days.

(21) Appl. No.: 14/289,207

(22) Filed: May 28, 2014

(65) Prior Publication Data

US 2015/0346225 A1    Dec. 3, 2015

(51) Int. Cl.
*G01N 33/84*    (2006.01)
*G01N 33/48*    (2006.01)
*G01N 33/52*    (2006.01)

(52) U.S. Cl.
CPC ............... *G01N 33/84* (2013.01); *G01N 33/48* (2013.01); *G01N 33/52* (2013.01); *G01N 2800/50* (2013.01); *Y10T 436/172307* (2015.01); *Y10T 436/25* (2015.01); *Y10T 436/25625* (2015.01)

(58) Field of Classification Search
CPC ....... G01N 33/48; G01N 33/50; G01N 33/52; G01N 2800/00; G01N 2800/50; G01N 2800/54; G01N 2800/7028; G01N 33/84; Y10Y 436/17; Y10Y 436/172307; Y10Y 436/25; Y10Y 436/25625; Y10T 436/17; Y10T 436/172307; Y10T 436/25; Y10T 436/25625

USPC ............. 436/63, 64, 106, 109, 164, 166, 174, 436/179
See application file for complete search history.

(56) References Cited

U.S. PATENT DOCUMENTS

| 9,110,029 | B2* | 8/2015 | O'Farrell | G01N 21/78 |
| 2005/0037514 | A1* | 2/2005 | Carron | G01N 21/658 436/171 |
| 2010/0012901 | A1* | 1/2010 | Falana et al. | 252/384 |
| 2013/0005044 | A1* | 1/2013 | Boss | G01N 31/22 436/109 |

OTHER PUBLICATIONS

Hesp et al. Clinical Physics and Physiological Measurement, vol. 3, No. 2, 1982, pp. 155-157.*
Buddha D. Paul et al.; Cyanide and Thiocyanate in Human Saliva by Gas Chromatography-Mass Spectrometry; Division of Forensic Toxicology, Office of the Armed Forces Medical Examiner, Armed Forces Institute of Pathology, Rockville, Maryland 20850; Journal of Analytical Toxicology, vol. 30, Oct. 2006; pp. 511-515.

* cited by examiner

*Primary Examiner* — Maureen Wallenhorst
(74) *Attorney, Agent, or Firm* — Dunlap Bennett & Ludwig PLLC

(57) ABSTRACT

A method of detecting a subject's cancer risk is provided. The method includes: gathering a sample of the subject's body water content via saliva; determining a ratio of cyanide within the subject's body water content and tissue saturation via saliva; providing a threshold cyanide ratio; comparing the ratio of cyanide within the subject's body water content and tissue saturation to the threshold cyanide ratio; and determining the patient's cancer risk based on the comparison of the ratio of cyanide within the subject's body water content to the threshold cyanide ratio.

3 Claims, 3 Drawing Sheets

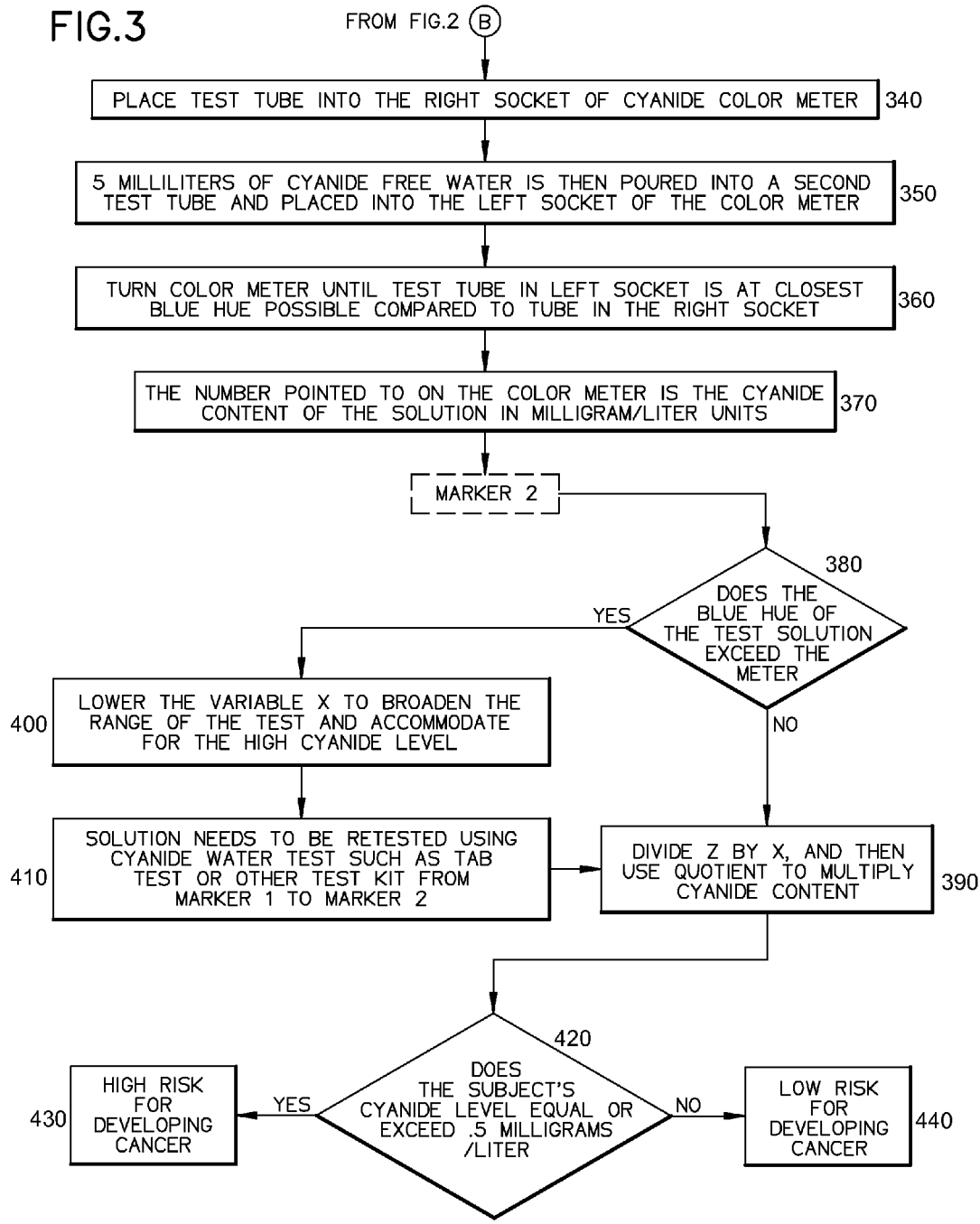

METHOD OF DETECTING A RISK OF CANCER

BACKGROUND OF THE INVENTION

The present invention relates to cancer detection and, more particularly, to a method of detecting the risk of acquiring cancer.

Cancer, known medically as malignant neoplasia, is a broad group of diseases involving unregulated cell growth. In cancer, cells divide and grow uncontrollably, forming malignant tumors, which may invade nearby parts of the body. The cancer may also spread to more distant parts of the body through the lymphatic system or bloodstream. Typically, if detected during the early stages, the cancer may be treatable. However, current forms of cancer detection and cancer risk detection are ineffective.

As can be seen, there is a need for an improved method of detecting the risk of acquiring cancer.

SUMMARY OF THE INVENTION

In one aspect of the present invention, a method of detecting a subject's cancer risk comprises the steps of: gathering a sample of the subject's body water content; determining a ratio of cyanide within the subject's body water content; providing a threshold cyanide ratio; comparing the ratio of cyanide within the subject's body water content to the threshold cyanide ratio; and determining the patient's cancer risk based on the comparison of the ratio of cyanide within the subject's body water content to the threshold cyanide ratio.

These and other features, aspects and advantages of the present invention will become better understood with reference to the following drawings, description and claims.

BRIEF DESCRIPTION OF THE DRAWINGS

FIG. 3 is a continuation of the flow chart of FIG. 2.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes screening for cyanide to test and determine a person's risk for developing cancer. The present invention is far more accurate than other methods, such as reviewing family history and/or testing a person's pH level.

The pre-test of the present invention relies on an empirical pattern discovered by determining that cancer patients have higher cyanide levels than those without cancer. The discovery of this pattern allows patients to be screened for cyanide and given an accurate idea of what their risk is for developing cancer and tracking states of remission. A threshold ratio of 0.5 milligrams/liter of cyanide was determined using the empirical data. The patient's cyanide levels are compared to the threshold ratio and using this comparison, patients with cyanide levels equal to or above 0.5 milligrams/liter have a high risk for developing cancer, and patients with levels of cyanide below 0.5 milligrams/liter have a low risk of developing cancer.

Using the present invention, patients are able to determine their risk of cancer by following a simple procedure that involves no harmful chemicals. Comparing the patient's cyanide level to the threshold ratio of 0.5 milligrams/liter of cyanide, where 0.5 milligrams/liter or more being at high risk while below 0.5 milligrams/liter being low risk, will allow people to effectively determine their risk for developing cancer. Knowing their risk will help people improve their health and lower their chances of developing cancer, effectively lowering the deaths related to cancer.

Figure 1:
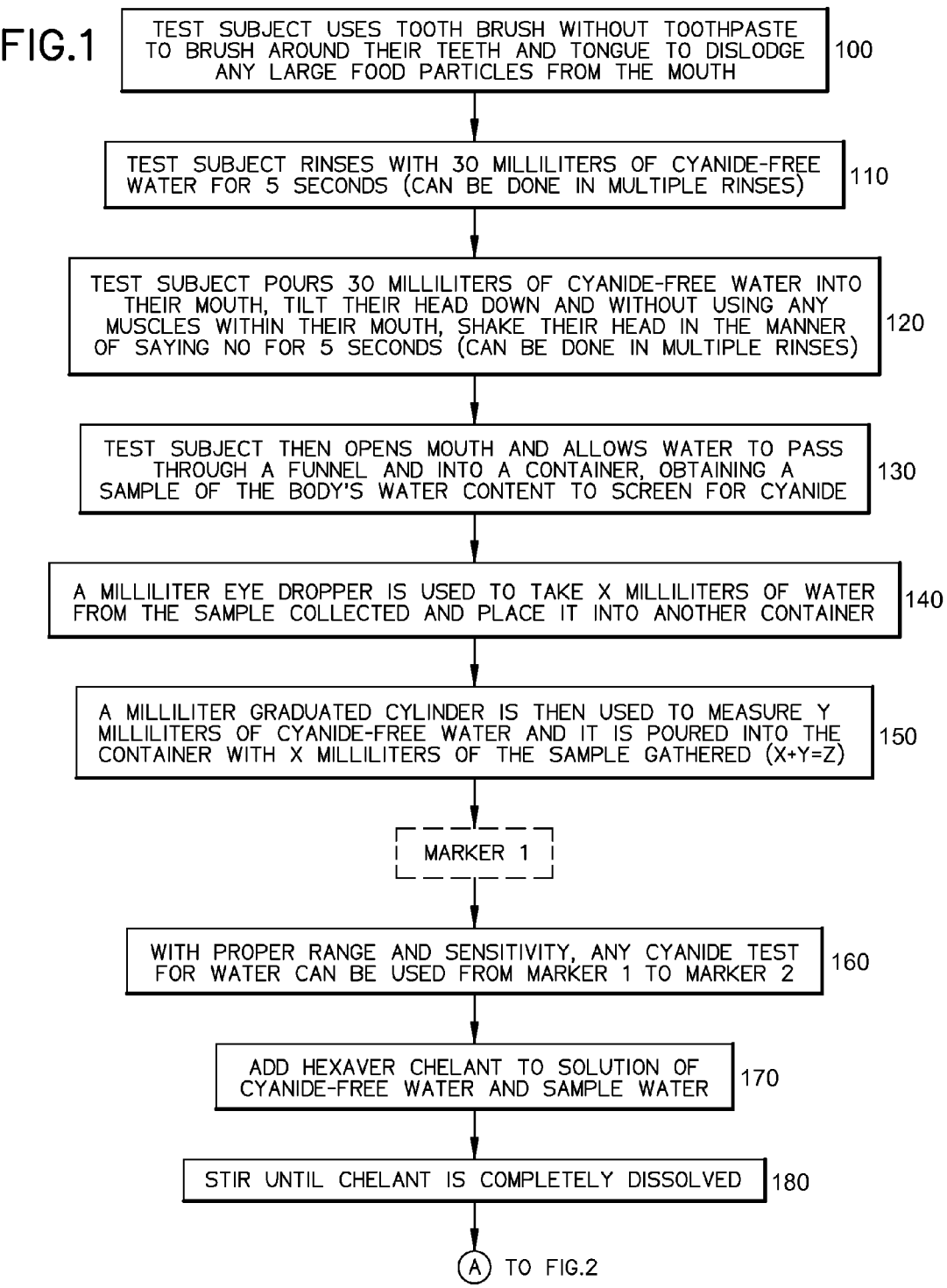
FIG. 1 is a flowchart of an embodiment of the present invention.
Figure 2:
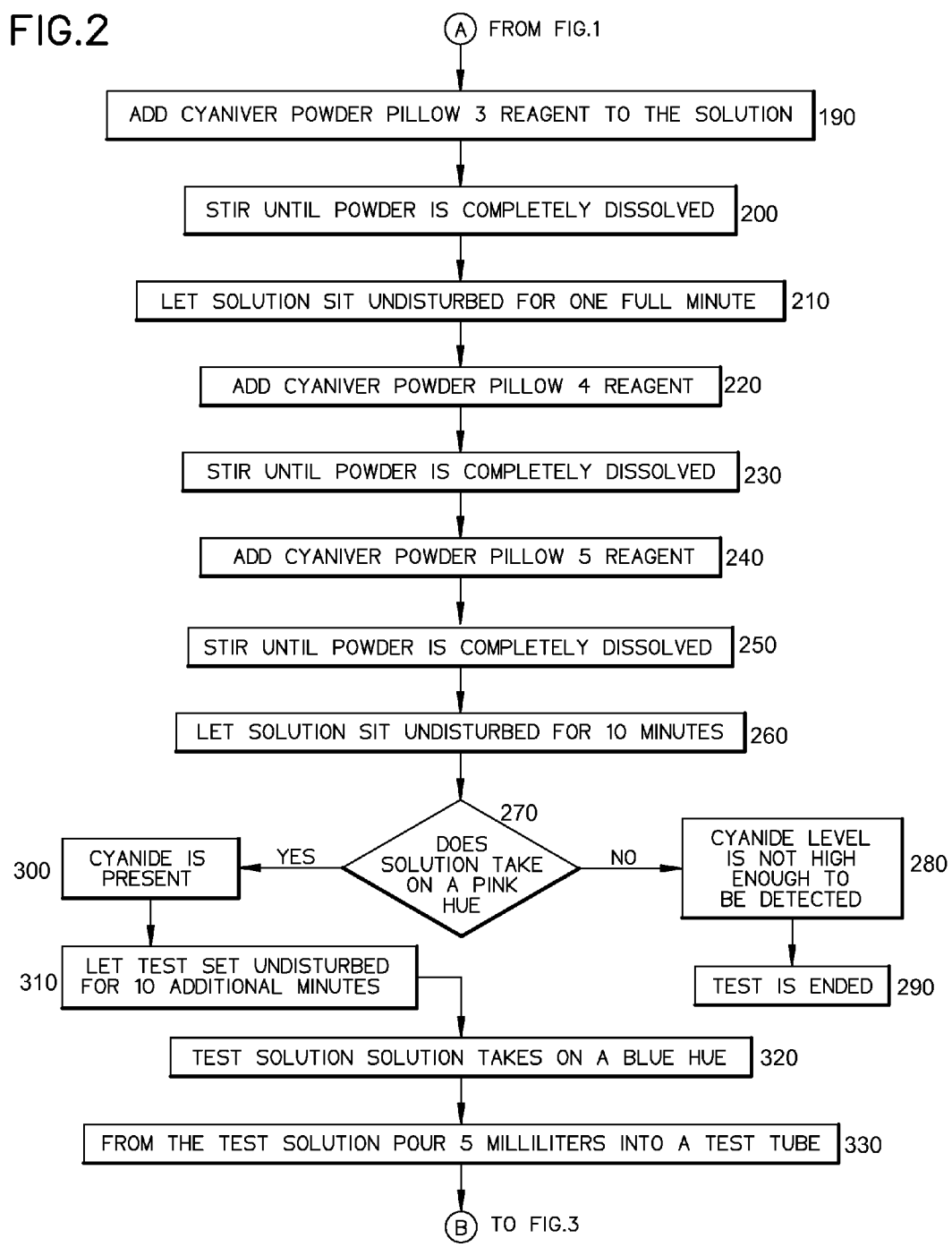
FIG. 2 is a continuation of the flow chart of FIG. 1.

Referring to FIGS. 1 through 3, the present invention includes a method of detecting a subject's cancer risk. The method includes: gathering a sample of the subject's body water content 100-150; determining a ratio of cyanide within the subject's body water content 310-370; providing a threshold cyanide ratio 420; comparing the ratio of cyanide within the subject's body water content to the threshold cyanide ratio 420; and determining the patient's cancer risk based on the comparison of the ratio of cyanide within the subject's body water content to the threshold cyanide ratio 420-440.

As mentioned above, the present invention may first include the step of gathering a sample of the subject's body water content. In certain embodiments, saliva may be gathered and used as the subject's body water content. The gathering of the sample of body water content via saliva may be performed using any suitable method, such as but not limited to, rinsing the patient's mouth with water, using a cotton swab, and the like. In certain embodiments, once the sample of the patient's body water content via saliva has been gathered, the saliva may be diluted so that a cyanide water test may easily detect an amount of cyanide within the body water content.

The following includes an exemplary method of properly gathering the body's water content via saliva from a patient. The test subject may use a toothbrush without toothpaste to brush around their teeth and tongue to dislodge any large food particles 100. The test subject may then rinse with about 30 milliliters of cyanide-free water for about five seconds (this step may be performed multiple times) 110. The test subject may pour 30 milliliters of cyanide-free water into their moth and shake their head for about five seconds (this step may be performed multiple times) 120. The test subject may then open their mouth and allow the water to pass through a funnel and into a container, obtaining a sample of the body's water content to screen for cyanide 130. A milliliter eye dropper may be used to take X amount of milliliters of water from the sample collected and place the X amount of water into a separate container 140. A milliliter graduated cylinder may then be used to measure Y milliliters of cyanide-free water and the Y amount of water may be poured into the container with the X amount of sample (X+Y=Z) 150.

Once the sample of the body's water content has been gathered, a cyanide test may be performed. Any cyanide test for water can be used 160. For example the following cyanide test may performed: add HEXAVER™ (cyclohexanediaminetetraacetic acid and disodium salt) chelant to solution of cyanide-free water and the sample 170; stir until chelant is completely dissolved 180; add CYANIVER™ powder pillow 3 reagent (sodium phosphate, dibasic, halane, potassium phosphate, and monobasic) to the solution 190; stir until powder is completely dissolved 200; let solution sit undisturbed for one full minute 210; add CYANIVER™ powder pillow 4 reagent (ascorbic acid, pyridine-3-nitrophthalic acid, and sodium sulfate) 220; stir until powder is completely dissolved 230; add CYANIVER™ powder pillow 5 reagent (potassium phosphate, monobasic, sodium sulfate, 3-methyl-1-phenyl-2-pyrazolin-5-one, sodium phosphate, and dibasic) 240; stir until powder is completely dissolved 250; and let solution sit undisturbed for about 10 minutes 260. If the solution takes on a pink hue 270, there is cyanide present 300. If the solution does not take on a pink hue 270, the cyanide level is not high enough to be detected 280 and the test is ended 290. This could mean that the variable X needs to be increased unless X=30, which means cyanide is not present.

A ratio of cyanide within the patient's body water content and tissue saturations is determined. In certain embodiments, the ratio may be determined using a cyanide color meter or any appropriate device. Using the cyanide color meter, the test solution from the cyanide test may set undisturbed for about an additional 10 minutes 310. The test solution may take on a blue hue 320. From the test solution, pour about 5 milliliters into a test tube 330. Place the test tube into the right socket of the cyanide color meter 340. Five milliliters of cyanide free water may then be poured into a second test tube and placed into the left socket of the color meter 350. The color meter may be turned until the test tube in the left socket is at the closest blue hue possible in comparison to the tube in the right socket 360. The number pointed to on the color meter is the cyanide content of the test solution in milligrams/liter units, thereby indicating the ratio of cyanide within the solution 370.

In certain embodiments, the blue hue of the test solution may exceed the cyanide color meter 380. If the blue hue of the test solution exceeds the color meter, the amount of milliliters of X during step 140 may be lowered to further dilute the cyanide within the mixture of step 150. The lowering of the variable X may broaden the range of the test and accommodate for high cyanide levels 400. The solution may then be retested using a cyanide water test such as a tab test or other test kit 410. Once the ratio of cyanide within the solution is determined, Z is divided by X and the quotient is multiplied by the cyanide content within the solution 390 to determine the cyanide ratio within the test subject.

A threshold of the cyanide ratio is provided. The threshold of the cyanide ratio was determined by gathering a plurality of test subjects, determining which of the test subjects either have cancer or end up getting cancer, and determining the amount of cyanide levels within those subjects, and comparing the cyanide levels to those who do not have cancer. The threshold level of cyanide may be 0.5 milligrams/liter. The ratio of cyanide within the patient's body water content and tissue saturation is compared to the threshold cyanide ratio. The patient's cancer risk is determined based on the comparison of the ratio of cyanide within the patient's body water content and tissue saturation to the threshold cyanide ratio. For example, if the test subjects have a cyanide level equal to or exceeding 0.5 milligrams/liter 420 the subject has a high risk for developing cancer or has cancer 430. If the test subjects have a cyanide level less than 0.5 milligrams/liter 420 the subject has a low risk for developing cancer 440.

With dilution testing, a test with a meter benchmark of 0.01 milligrams/liter and a range of 0 to 0.3 milligrams/liter may be efficient to test a person for cyanide. However, the use of a test strip or any other method may yield results that are not as accurate as the above method because they will most likely be unable to read cyanide accurately within a 0.01 milligrams/liter benchmark. An altered test may be created that involves lowering the quantity of chemicals used within the test and creating a new color meter to accommodate for the increased range of the new test. This new test may result in the simplifying of the test method by disposing of the dilution testing.

Below is a table 1 showing test subjects classified under the Cancer History and State of Health category having cyanide levels above or equal to 0.5 milligrams/liter. Two test subjects under the Cancer category were not above the threshold levels. However, these patients were undergoing treatment and were soon classified as in remission. Test subjects within the Remission History and State of Health category had results showing that some were still at risk of developing cancer, while others were not at risk and therefore not likely to develop cancer again. Subjects who were in the Healthy history category included results of subjects having a high risk for developing cancer and subjects having a low risk for developing cancer.

TABLE 1

| History | Smoking Habits | pH Level | Cyanide Level (mg/L) | State of Health |
|---|---|---|---|---|
| Cancer | Never Smoked | 7.5 | 1.25 | Cancer |
| Cancer | Ex-Smoker | 6.5 | 1.4 | Cancer |
| Cancer | Never Smoked | 6 | 1.5 | Cancer |
| Cancer | Never Smoked | 7.5 | 0.75 | Cancer |
| Cancer | Smoker | 6 | 1.5 | Cancer |
| Cancer | Ex-Smoker | 6 | 1.25 | Cancer |
| Cancer | Ex-Smoker | 8 | 3 | Cancer |
| Cancer | Ex-Smoker | 7.5 | 0.4 | Cancer |
| Cancer | Smoker | 7 | 0.9 | Cancer |
| Cancer | Ex-Smoker | 8.5 | 0.2 | Cancer |
| Cancer | Never Smoked | 7 | 0.1 | Cancer |
| Cancer | Smoker | 6 | 0.75 | Cancer |
| Cancer | Ex-Smoker | 7 | 0.8 | Cancer |
| Cancer | Ex-Smoker | Inconclusive | 1.8 | Cancer |
| Cancer | Ex-Smoker | 8 | 1 | Cancer |
| Cancer | Never Smoked | 6.5 | 0.75 | Cancer |
| Cancer | Never Smoked | 7 | 0.5 | Cancer |
| Cancer | Never Smoked | 8 | 2 | Cancer |
| Cancer | Smoker | 6 | 2.25 | Cancer |
| Cancer | Never Smoked | 7 | 0.4 | Cancer |
| Cancer | Smoker | 6 | 1.1 | Cancer |
| Cancer | Never Smoked | 6 | 0.5 | Cancer |
| Healthy | Never Smoked | 7 | 0.6 | High Risk |
| Remission | Never Smoked | 7 | 1.5 | High Risk |
| Remission | Ex-Smoker | 7 | 1.15 | High Risk |
| Healthy | Smoker | 6 | 1.5 | High Risk |
| Healthy | Never Smoked | 7 | 0.6 | High Risk |
| Healthy | Ex-Smoker | 6 | 1 | High Risk |
| Healthy | Smoker | 6 | 1.5 | High Risk |
| Healthy | Smoker | 6 | 1.5 | High Risk |
| Healthy | Never Smoked | 7 | 0.84 | High Risk |
| Healthy | Ex-Smoker | 6 | 0.9 | High Risk |
| Remission | Ex-Smoker | 8.5 | 1.5 | High Risk |
| Healthy | Ex-Smoker | 8 | 0.6 | High Risk |
| Healthy | Ex-Smoker | 5 | 0.9 | High Risk |
| Remission | Never Smoked | 8 | 0.65 | High Risk |
| Remission | Ex-Smoker | 7 | 0.7 | High Risk |
| Healthy | Ex-Smoker | 6 | 0.05 | Low Risk |
| Healthy | Never Smoked | 6.5 | 0.1 | Low Risk |
| Healthy | Never Smoked | 6.5 | 0.35 | Low Risk |
| Healthy | Never Smoked | 8 | 0.15 | Low Risk |
| Healthy | Ex-Smoker | 7 | 0.1 | Low Risk |
| Healthy | Never Smoked | 7 | 0.4 | Low Risk |
| Remission | Never Smoked | 6 | 0.45 | Low Risk |
| Remission | Never Smoked | 6 | 0.25 | Remission |
| Remission | Never Smoked | 6 | 0.3 | Remission |
| Remission | Never Smoked | 6 | 0.3 | Remission |

It should be understood, of course, that the foregoing relates to exemplary embodiments of the invention and that modifications may be made without departing from the spirit and scope of the invention as set forth in the following claims.

What is claimed is:

1. A method of determining a subject's cyanide level, said method comprising the steps of:
   removing food particles from the subject's mouth;

rinsing the subject's mouth with a first volume of cyanide-free water;

adding a second volume of cyanide-free water to the subject's mouth after said rinsing;

collecting a portion of the second volume of cyanide-free water from the subject's mouth, wherein said portion has a third volume X;

diluting the collected portion of cyanide-free water with a fourth volume Y of cyanide-free water to form a test sample having a fifth volume Z;

contacting the test sample with reagents suitable to detect cyanide if present in the test sample;

detecting, as a result of said contacting, an amount of cyanide in milligrams/liter if present in the test sample; and determining the subject's cyanide level in milligrams/liter by dividing Z by X to equal a quotient and multiplying said quotient by the milligrams/liter of cyanide detected in said test sample.

2. The method of claim 1, wherein said removing comprises:

brushing the subject's teeth using a toothbrush without using toothpaste.

3. The method of claim 1, wherein said reagents cause a colorometric change in the test sample during said contacting if cyanide is present, and said detecting comprises:

placing the contacted test sample in a cyanide color meter, and obtaining a colormetric reading of the contacted test sample from the color meter, wherein said colormetric reading provides the amount of cyanide in milligrams/liter present in the test sample.

\* \* \* \* \*